United States Patent [19]

Froning et al.

[11] Patent Number: 4,505,709

[45] Date of Patent: Mar. 19, 1985

[54] LIQUID TRANSFER DEVICE

[76] Inventors: Edward C. Froning, P.O. Box 1768, Rancho Santa Fe, Calif. 92067; Gregory S. Graham, c/o Today's Machinery & Design, 2368 Eastman, #14, Ventura, Calif. 93002

[21] Appl. No.: 468,473

[22] Filed: Feb. 22, 1983

[51] Int. Cl.[3] .......... A61M 1/00

[52] U.S. Cl. .......... 604/411

[58] Field of Search .......... 604/411, 412, 413, 414, 604/415

[56] References Cited

U.S. PATENT DOCUMENTS 2,415,871 2/1947 De Woody .......... 604/415

3,882,909 5/1975 Ogle .......... 604/414

4,262,671 4/1981 Kersten .......... 604/411

FOREIGN PATENT DOCUMENTS 1105576 12/1955 France .......... 604/411

*Primary Examiner*—John D. Yasko
*Attorney, Agent, or Firm*—Julian Caplan

[57] ABSTRACT

The device is used to transfer liquids such as pharmaceuticals from a container having a stopper of rubber or other material which can be punctured with a needle to a syringe. The device has a plug which is pressed down on the stopper and on the bottom on the plug are two needles. The first needle is long enough to extend near the bottom of the container and has a connection through the plug to a fitting to which the syringe is connected. By raising the plunger in the syringe, liquid is drawn from the container. The second needle is preferably shorter than the first and communicates with the atmosphere through a second connection in the plug. Thus air is admitted into the container to replace the liquid withdrawn into the syringe. A micro-pore filter in the second connection may be used to prevent contamination of the container.

4 Claims, 3 Drawing Figures

LIQUID TRANSFER DEVICE

This invention relates to a new and improved liquid transfer device to facilitate use of of a luer syringe to withdraw liquid from a conventional rubber stoppered container for pharmaceuticals and other substances.

A conventional container for pharmaceuticals and other substances is airtight, being closed by a rubber or rubber-like stopper which is permeable in that a syringe needle may be forced through the stopper as the means for withdrawing liquid therefrom. Since the quantity of liquid in the container is ordinarily considerably greater than one dosage, the container is used repeatedly. In an operating room, such a container is considered non-sterile and is located outside the perimeter of the sterile area of the operation.

Heretofore, during operating procedures, the surgeon, nurse, physician or physician's designate used a syringe to withdraw the required dosage of liquid from such a container, However, the syringe and the surgeon are in the sterile area of the operating room while the container is non-sterile. This fact, plus other problems hereinafter mentioned, have caused considerable difficulties in the mechanics of withdrawing liquids from the container.

One principal difficulty which is obviated by the present invention is the maneuvering required when the container is held by a "non-sterile" nurse and the syringe by a surgeon. The sterile personnel cannot contact either the non-sterile container or the non-sterile nurse. To insert the needle into the container and to withdraw the necessary quantity of liquid is thus a two-person effort which may be very awkward and time consuming.

Another difficulty in prior techniques is that the length of the needle may be less that the height of the bottle, requiring tilting the container after a quantity of the liquid has been depleted. This again complicates the two-person effort of the nurse holding the container and the surgeon holding the syringe.

Since the container is airtight, liquid withdrawn must be replaced with air. Thus the syringe is normally initially filled with air and after the needle is inserted in the stopper the plunger of the syringe is depressed, forcing air into the container and permitting subsequent withdrawal of an amount of liquid less than the amount of air introduced. Such a maneuver may result in non-sterile air being introduced into the container. Another problem is that the quantity of liquid required for injection into the patient may exceed the amount of liquid which may be removed with one cycle of the syringe plunger. When the latter situation has occurred, it has been customary to withdraw a portion of the necessary liquid by one cycle of the syringe plunger and discharge it into a beaker and then repeat the cycle one or more times. When the necessary quantity is in the beaker, it is drawn into the syringe. This again is an awkward and time consuming series of maneuvers. Furthermore, in some instances, the beaker may tip over unless great care is exercised.

In certain operations, long and, frequently, curved needles are required. Use of such needles to withdraw liquid from a container additionally complicates all of the foregoing problems.

The present invention provides a sterile device which is attached to the container and has two needles, a long needle which extends to adjacent the bottom of the container for withdrawal of liquid and which is attached to the syringe only while the liquid is being withdrawn and a second needle which permits air to enter the container to replace the liquid to be withdrawn. A micro-pore filter may be inserted in the passageway through which air enters the second needle to filter out foreign particles in the air which are large enough to support germs.

Thus, in accordance with the present invention, the non-sterile container is placed on a table adjacent the sterile area of the operating room, the sterile device which is the subject of this invention is attached to the container by pushing the device downward until both needles penetrate the rubber stopper and then attaching the syringe which will be used for the injection to the device. The skirt of the device has a flange which assists in pushing the needle down. The flange also acts as a shield to prevent the surgeon's hand from contacting the non-sterile container. The surgeon then withdraws the required quantity of liquid from the container, removes the syringe from the device and attaches the conventional syringe needle which will be used for injecting the liquid into the patient.

The maneuering heretofore required to be performed by the non-sterile nurse and the surgeon to accomplish withdrawal of liquid from the container is almost entirely eliminated with consequent elimination of danger of contamination and spillage. Accordingly, operating room personnel may concentrate attention on the operation itself rather than the mechanics of filling the syringe.

Other objects of the present invention will become apparent upon reading the following specification and referring to the accompanying drawings in which similar characters of reference represent corresponding parts in each of the several views.

Figure 1:
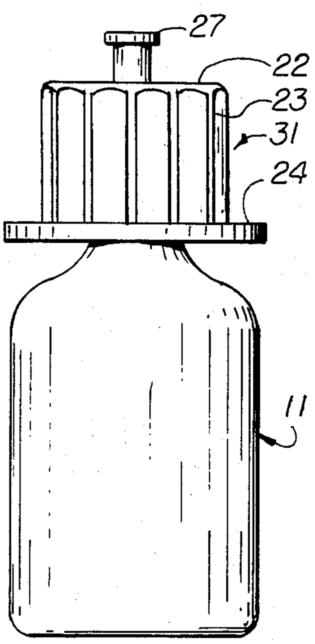
FIG. 1 is a front elevational view of the device of the present invention installed on a conventional pharmaceutical container.
Figure 2:
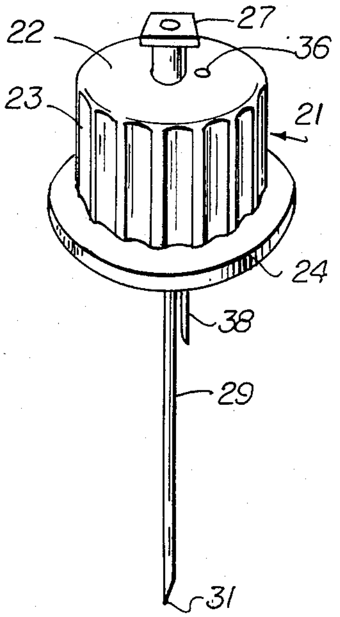
FIG. 2 is a perspective view of the device.
Figure 3:
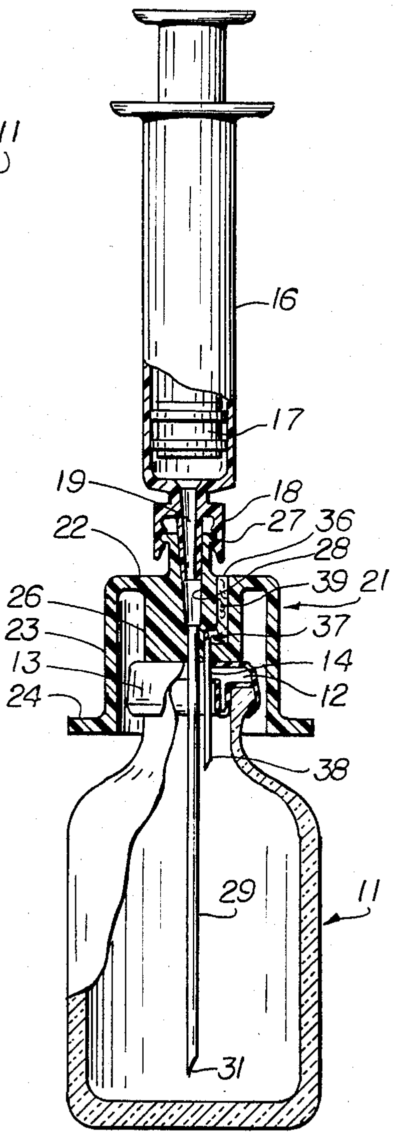
FIG. 3 is an elevational view partially broken away to reveal internal construction showing the device installed on a container and with a syringe attached thereto.

The present invention is used with a container 11 of conventional type, hermetically sealed with a stopper 12 which is of a rubber or rubber-like material and is held on the container 11 by a metal band 13. The top 14 of the stopper 12 is permeable by a conventional syringe needle.

Also used with the device is a luer-type syringe 16 having a plunger 17 reciprocable therein and also formed with a female fitting 18 normally used for interlocking with a conventional syringe needle (not shown). A tapered protruding connector 19 serves as a conduit between the chamber of the syringe 16 and the conventional needle. It will be understood that the present invention may be used with other types of syringe constructions by modifications of the structure of the device which will readily occur to one skilled in the art.

The transfer device 21 has a top 22 from which depends a skirt 23 having a peripheral flange 24. The inside of the skirt is larger than the band 13. Centrally disposed below the top 22 is a plug-like body 26 and above the top 22 is a male fitting 27 which interfits with the fitting 18 by relative twisting of the two fittings. A downward tapered socket 28 is formed in the fitting 27 and the plug 26 to receive the connector 19 of syringe 16. Below socket 28 and communicating therewith is an elongated needle 29 having a sharp point 31.

Offset laterally from fitting 27 is an opening 36 in top 22 which extends into the plug 26 and has an offset 37 which establishes communication with a second needle 38, preferably shorter than the needle 31. If desired, a micropore filter material 39 may be inserted in the passage 36 to filter out any large contaminating particles in the air which might support bacteria which, upon entering the container 11, might contaminate the same.

In use in an operating room, the container 11 is placed on any suitable support conveniently at hand to the surgeon. The sterile wrapper is then removed from the device 21 and the point 31 of needle 29 inserted in the permeable top 14 of stopper 12. The flange 24 provides a convenient means for pushing the device 21 downward until both needles 29 and 38 have penetrated the stopper and the tip 31 is adjacent the bottom of the container 11. The flange also shields the surgeon's fingers from contact with the non-sterile container. Thereupon, the sterile syringe 16 is attached to the device 21 by inserting the point 19 in the socket 28 and turning so that the fittings 18 and 27 interlock. Thereupon, the surgeon raises the plunger 17 to withdraw liquid from the bottom of the container 11, the volume of liquid withdrawn being replaced by air which enters through the opening 36 duct 37 and second needle 38. As much liquid as may be required may be withdrawn from the container 11 in one upward movement of the plunger 17 as contrasted with the maneuvering normally required in an operating room which has heretofore been described.

What is claimed is:

1. A device for use with a syringe for withdrawal of liquid from a container have a needle-pervious stopper comprising a body having a fitting on its top shaped for connection to a mating fitting on a syringe, said body being formed with a socket extending through said body, said body having a flat bottom end, a pointed first needle depending from said bottom end for puncturing said stopper communicating with said socket and a second needle depending from said bottom end to permit entry of air through said body and said stopper to replace, with air, liquid drawn out through said first needle and socket, said first and second needles comprising the only projection from said bottom end, and an opening to atmosphere formed in said body communicating with said second needle.

2. A device according to claim 1 which further comprises a filter associated with said second needle to filter out particles large enough to support bacteria.

3. A device according to to claim 1 in which said fitting further comprises an inward tapering socket extending downward through said fitting and the upper end of said body and communicating with said first needle, said socket being shaped to receive the tapered protruding connector of said syringe.

4. A device according to claim 1 which further comprises a peripheral disc extending outward from the top of said body, a skirt depending from said disc and a peripheral flange on said skirt, said peripheral flange being lower than the bottom end of said body.

* * * * *